US009968401B2

(12) United States Patent
Manley et al.

(10) Patent No.: US 9,968,401 B2
(45) Date of Patent: May 15, 2018

(54) MICROWAVE ABLATION SYSTEM WITH DIELECTRIC TEMPERATURE PROBE

(71) Applicant: COVIDIEN LP, Mansfield, MA (US)

(72) Inventors: Prakash Manley, Lafayette, CO (US); Joseph D. Brannan, Erie, CO (US)

(73) Assignee: Covidien LP, Mansfield, MA (US)

( * ) Notice: Subject to any disclaimer, the term of this patent is extended or adjusted under 35 U.S.C. 154(b) by 276 days.

(21) Appl. No.: 14/539,326

(22) Filed: Nov. 12, 2014

(65) Prior Publication Data

US 2015/0073403 A1    Mar. 12, 2015

Related U.S. Application Data

(63) Continuation of application No. 12/642,623, filed on Dec. 18, 2009, now Pat. No. 8,882,759.

(51) Int. Cl.
| | | |
|---|---|---|
| *A61B 18/12* | (2006.01) | |
| *A61B 18/18* | (2006.01) | |
| *A61B 17/00* | (2006.01) | |
| *A61B 18/00* | (2006.01) | |

(52) U.S. Cl.
CPC ............ *A61B 18/1815* (2013.01); *A61B 2017/00084* (2013.01); *A61B 2018/00577* (2013.01); *A61B 2018/00648* (2013.01); *A61B 2018/00791* (2013.01); *A61B 2018/00875* (2013.01); *A61B 2018/1869* (2013.01)

(58) Field of Classification Search
CPC ...... A61B 18/1815; A61B 2018/00636; A61B 2018/00642; A61B 2018/00648; A61B 2018/00684; A61B 2018/00702; A61B 2018/00708; A61B 2018/00791; A61B 2018/00839; A61B 2018/00875; A61B 2018/1869; A61B 2018/00577
USPC .................... 606/33, 34, 38, 41, 42
See application file for complete search history.

(56) References Cited

U.S. PATENT DOCUMENTS

| 4,204,549 A | 5/1980 | Paglione |
|---|---|---|
| 4,291,708 A | 9/1981 | Frei et al. |
| D263,020 S | 2/1982 | Rau, III |

(Continued)

FOREIGN PATENT DOCUMENTS

| DE | 390937 C | 3/1924 |
|---|---|---|
| DE | 1099658 B | 2/1961 |

(Continued)

OTHER PUBLICATIONS

European Search Report EP 04013772 dated Apr. 11, 2005.

(Continued)

*Primary Examiner* — Thomas Giuliani

(57) ABSTRACT

An electromagnetic surgical ablation system having a generator adapted to selectively provide surgical ablation energy to an ablation probe, and methods of operating same, are disclosed. The system includes a controller operatively coupled to the generator, and a tissue sensor probe operatively coupled to the controller. The tissue sensor provides a tissue temperature and at least one tissue dielectric property to the controller. During an electromagnetic tissue ablation procedure, the controller monitors tissue temperature and the at least one tissue dielectric property to determine tissue status, and to activate and deactivate the generator in accordance therewith.

8 Claims, 9 Drawing Sheets

(56) References Cited

U.S. PATENT DOCUMENTS

| | | |
|---|---|---|
| 4,402,309 A | 9/1983 | Harrison |
| 4,458,694 A | 7/1984 | Sollish et al. |
| 4,507,602 A | 3/1985 | Aguirre |
| 4,510,437 A | 4/1985 | Iskander |
| 4,539,640 A | 9/1985 | Fry et al. |
| 4,583,869 A | 4/1986 | Chive et al. |
| D295,893 S | 5/1988 | Sharkany et al. |
| D295,894 S | 5/1988 | Sharkany et al. |
| 4,765,179 A | 8/1988 | Fuller et al. |
| 4,780,661 A | 10/1988 | Bolomey et al. |
| 4,798,215 A | 1/1989 | Turner |
| 4,805,621 A | 2/1989 | Heinze et al. |
| 5,025,810 A | 6/1991 | Kikuchi et al. |
| 5,033,478 A | 7/1991 | Kikuchi et al. |
| RE33,791 E | 1/1992 | Carr |
| 5,143,079 A | 9/1992 | Frei et al. |
| 5,148,814 A | 9/1992 | Kikuchi et al. |
| 5,227,730 A | 7/1993 | King et al. |
| 5,233,306 A | 8/1993 | Misra |
| 5,334,941 A | 8/1994 | King |
| 5,344,435 A | 9/1994 | Turner et al. |
| 5,364,392 A | 11/1994 | Warner et al. |
| 5,385,148 A | 1/1995 | Lesh et al. |
| 5,452,716 A | 9/1995 | Clift |
| 5,502,394 A | 3/1996 | Piau |
| 5,503,150 A | 4/1996 | Evans |
| 5,508,203 A | 4/1996 | Fuller et al. |
| 5,531,676 A | 7/1996 | Edwards et al. |
| 5,540,684 A | 7/1996 | Hassler, Jr. |
| 5,549,639 A | 8/1996 | Ross |
| 5,643,257 A | 7/1997 | Cohen et al. |
| 5,658,282 A | 8/1997 | Daw et al. |
| 5,713,942 A | 2/1998 | Stern et al. |
| 5,744,971 A | 4/1998 | Chan et al. |
| 5,776,176 A | 7/1998 | Rudie |
| 5,792,668 A | 8/1998 | Fuller et al. |
| 5,800,494 A | 9/1998 | Campbell et al. |
| 5,810,803 A | 9/1998 | Moss et al. |
| 5,821,410 A | 10/1998 | Xiang et al. |
| 5,829,437 A | 11/1998 | Bridges |
| 5,861,021 A | 1/1999 | Thome et al. |
| 5,869,973 A | 2/1999 | Nosov |
| 5,900,618 A | 5/1999 | Anlage et al. |
| 5,902,251 A | 5/1999 | vanHooydonk |
| 5,904,709 A | 5/1999 | Arndt et al. |
| 5,921,982 A | 7/1999 | Lesh et al. |
| 5,957,969 A | 9/1999 | Warner et al. |
| 6,016,452 A | 1/2000 | Kasevich |
| 6,026,323 A | 2/2000 | Skladnev et al. |
| 6,026,331 A | 2/2000 | Feldberg et al. |
| 6,053,909 A | 4/2000 | Shadduck |
| 6,054,693 A | 4/2000 | Barmatz et al. |
| D424,694 S | 5/2000 | Tetzlaff et al. |
| D425,201 S | 5/2000 | Tetzlaff et al. |
| 6,061,589 A | 5/2000 | Bridges et al. |
| 6,104,959 A | 8/2000 | Spertell |
| 6,109,268 A | 8/2000 | Thapliyal et al. |
| 6,112,123 A | 8/2000 | Kelleher et al. |
| 6,123,702 A | 9/2000 | Swanson et al. |
| 6,134,476 A | 10/2000 | Arndt et al. |
| 6,175,768 B1 | 1/2001 | Arndt et al. |
| 6,179,832 B1 | 1/2001 | Jones et al. |
| 6,201,400 B1 | 3/2001 | Lind |
| 6,230,060 B1 | 5/2001 | Mawhinney |
| 6,231,569 B1 | 5/2001 | Bek et al. |
| 6,232,760 B1 | 5/2001 | Eckert |
| 6,233,479 B1 | 5/2001 | Haddad et al. |
| 6,233,490 B1 | 5/2001 | Kasevich |
| 6,275,738 B1 | 8/2001 | Kasevich et al. |
| 6,293,941 B1 | 9/2001 | Strul et al. |
| D449,886 S | 10/2001 | Tetzlaff et al. |
| 6,309,386 B1 | 10/2001 | Bek |
| 6,370,426 B1 | 4/2002 | Campbell et al. |
| D457,958 S | 5/2002 | Dycus et al. |
| D457,959 S | 5/2002 | Tetzlaff et al. |
| 6,383,183 B1 | 5/2002 | Sekino et al. |
| 6,402,742 B1 | 6/2002 | Blewett et al. |
| 6,413,255 B1 | 7/2002 | Stern |
| 6,488,678 B2 | 12/2002 | Sherman |
| 6,496,738 B2 | 12/2002 | Carr |
| 6,524,308 B1 | 2/2003 | Muller et al. |
| 6,537,272 B2 | 3/2003 | Christopherson et al. |
| 6,546,292 B1 | 4/2003 | Steinhaus et al. |
| 6,577,903 B1 | 6/2003 | Cronin et al. |
| 6,597,185 B1 | 7/2003 | Talanov et al. |
| 6,610,054 B1 | 8/2003 | Edwards et al. |
| 6,629,974 B2 | 10/2003 | Penny et al. |
| 6,635,055 B1 | 10/2003 | Cronin |
| 6,648,883 B2 | 11/2003 | Francischelli et al. |
| 6,657,173 B2 | 12/2003 | Flugstad et al. |
| 6,677,762 B1 | 1/2004 | Adenot et al. |
| 6,690,976 B2 | 2/2004 | Fenn et al. |
| 6,692,492 B2 | 2/2004 | Simpson et al. |
| 6,725,095 B2 | 4/2004 | Fenn et al. |
| 6,730,079 B2 | 5/2004 | Lovewell |
| 6,768,925 B2 | 7/2004 | Fenn et al. |
| 6,784,405 B2 | 8/2004 | Flugstad et al. |
| 6,788,977 B2 | 9/2004 | Fenn et al. |
| D496,997 S | 10/2004 | Dycus et al. |
| 6,807,444 B2 | 10/2004 | Tu et al. |
| 6,807,446 B2 | 10/2004 | Fenn et al. |
| D499,181 S | 11/2004 | Dycus et al. |
| 6,813,515 B2 | 11/2004 | Hashimshony |
| 6,818,000 B2 | 11/2004 | Muller et al. |
| 6,849,073 B2 | 2/2005 | Hoey et al. |
| 6,850,804 B2 | 2/2005 | Eggers et al. |
| 6,866,624 B2 | 3/2005 | Chornenky et al. |
| 6,939,344 B2 | 9/2005 | Kreindel |
| 6,939,346 B2 | 9/2005 | Kannenberg et al. |
| 6,955,675 B2 | 10/2005 | Jain |
| 6,979,328 B2 | 12/2005 | Baerveldt et al. |
| 6,989,010 B2 | 1/2006 | Francischelli et al. |
| 6,993,394 B2 | 1/2006 | Eggers et al. |
| 7,001,415 B2 | 2/2006 | Hooven |
| 7,004,941 B2 | 2/2006 | Tvinnereim et al. |
| 7,048,756 B2 | 5/2006 | Eggers et al. |
| 7,056,011 B2 | 6/2006 | Pesach |
| D525,361 S | 7/2006 | Hushka |
| 7,074,217 B2 | 7/2006 | Strul et al. |
| 7,090,672 B2 | 8/2006 | Underwood et al. |
| D531,311 S | 10/2006 | Guerra et al. |
| D533,942 S | 12/2006 | Kerr et al. |
| 7,146,210 B2 | 12/2006 | Palti |
| D535,027 S | 1/2007 | James et al. |
| 7,160,296 B2 | 1/2007 | Pearson et al. |
| 7,169,144 B2 | 1/2007 | Hoey et al. |
| 7,184,824 B2 | 2/2007 | Hashimshony |
| D541,418 S | 4/2007 | Schechter et al. |
| 7,207,989 B2 | 4/2007 | Pike, Jr. et al. |
| D541,938 S | 5/2007 | Kerr et al. |
| 7,247,155 B2 | 7/2007 | Hoey et al. |
| 7,282,049 B2 | 10/2007 | Orszulak et al. |
| 7,294,127 B2 | 11/2007 | Leung et al. |
| 7,304,488 B2 | 12/2007 | Gleason et al. |
| 7,311,703 B2 | 12/2007 | Turovskiy et al. |
| 7,330,041 B2 | 2/2008 | McFadden |
| D564,662 S | 3/2008 | Moses et al. |
| 7,341,586 B2 | 3/2008 | Daniel et al. |
| 7,344,533 B2 | 3/2008 | Pearson et al. |
| 7,367,972 B2 | 5/2008 | Francischelli et al. |
| 7,393,352 B2 | 7/2008 | Berube |
| 7,410,485 B1 | 8/2008 | Fink et al. |
| 7,417,446 B2 | 8/2008 | Hayden et al. |
| 7,419,487 B2 | 9/2008 | Johnson et al. |
| 7,449,899 B2 | 11/2008 | Campbell et al. |
| 7,452,358 B2 | 11/2008 | Stern et al. |
| 7,453,276 B2 | 11/2008 | Hayden et al. |
| 7,467,015 B2 | 12/2008 | van der Weide |
| 7,473,251 B2 | 1/2009 | Knowlton et al. |
| 7,479,141 B2 | 1/2009 | Kleen et al. |
| 7,483,755 B2 | 1/2009 | Ingle et al. |
| 8,882,759 B2 | 11/2014 | Manley et al. |
| 2001/0008966 A1 | 7/2001 | Arndt et al. |
| 2001/0008967 A1 | 7/2001 | Sherman |

(56) References Cited

U.S. PATENT DOCUMENTS

| | | |
|---|---|---|
| 2002/0049483 A1 | 4/2002 | Knowlton |
| 2002/0087151 A1 | 7/2002 | Mody et al. |
| 2002/0091427 A1 | 7/2002 | Rappaport et al. |
| 2002/0128636 A1 | 9/2002 | Chin et al. |
| 2002/0135103 A1 | 9/2002 | Odorzynski et al. |
| 2002/0156471 A1 | 10/2002 | Stern et al. |
| 2003/0004454 A1 | 1/2003 | Fenn et al. |
| 2003/0050630 A1 | 3/2003 | Mody et al. |
| 2003/0050631 A1 | 3/2003 | Mody et al. |
| 2003/0060818 A1 | 3/2003 | Kannenberg et al. |
| 2003/0069575 A1 | 4/2003 | Chin et al. |
| 2003/0069619 A1 | 4/2003 | Fenn et al. |
| 2003/0073989 A1 | 4/2003 | Hoey et al. |
| 2003/0083654 A1 | 5/2003 | Chin et al. |
| 2003/0097162 A1 | 5/2003 | Kreindel |
| 2003/0109778 A1 | 6/2003 | Rashidi |
| 2003/0109868 A1 | 6/2003 | Chin et al. |
| 2003/0130711 A1 | 7/2003 | Pearson et al. |
| 2003/0163128 A1 | 8/2003 | Patil et al. |
| 2003/0187366 A1 | 10/2003 | Hashimshony |
| 2003/0212394 A1 | 11/2003 | Pearson et al. |
| 2004/0049251 A1 | 3/2004 | Knowlton |
| 2004/0122494 A1 | 6/2004 | Eggers et al. |
| 2004/0138652 A1 | 7/2004 | Berube |
| 2004/0138653 A1 | 7/2004 | Dabney et al. |
| 2004/0230263 A1 | 11/2004 | Samulski |
| 2005/0015081 A1 | 1/2005 | Turovskiy et al. |
| 2006/0020312 A1 | 1/2006 | Eggers et al. |
| 2006/0020313 A1 | 1/2006 | Eggers et al. |
| 2006/0030912 A1 | 2/2006 | Eggers et al. |
| 2006/0030913 A1 | 2/2006 | Eggers et al. |
| 2006/0030914 A1 | 2/2006 | Eggers et al. |
| 2006/0106375 A1 | 5/2006 | Werneth et al. |
| 2006/0217694 A1 | 9/2006 | Chin et al. |
| 2007/0050001 A1 | 3/2007 | Luttich et al. |
| 2007/0056960 A1 | 3/2007 | Bell |
| 2007/0088413 A1 | 4/2007 | Weber et al. |
| 2007/0106289 A1 | 5/2007 | O'Sullivan |
| 2007/0106349 A1 | 5/2007 | Karni et al. |
| 2007/0142829 A1 | 6/2007 | Ahn et al. |
| 2007/0156211 A1 | 7/2007 | Ferren et al. |
| 2007/0173811 A1 | 7/2007 | Couture et al. |
| 2007/0179491 A1* | 8/2007 | Kratoska ............ A61B 18/1477 606/32 |
| 2007/0185554 A1 | 8/2007 | Appling et al. |
| 2007/0191825 A1 | 8/2007 | Cronin et al. |
| 2007/0198006 A1 | 8/2007 | Prakash et al. |
| 2007/0203551 A1 | 8/2007 | Cronin et al. |
| 2007/0225697 A1 | 9/2007 | Shroff et al. |
| 2007/0233057 A1 | 10/2007 | Konishi |
| 2007/0250051 A1 | 10/2007 | Gaston et al. |
| 2007/0265606 A1 | 11/2007 | DeBenedictis et al. |
| 2007/0270924 A1 | 11/2007 | McCann et al. |
| 2007/0284034 A1 | 12/2007 | Fathi et al. |
| 2007/0296435 A1 | 12/2007 | Eldridge et al. |
| 2007/0299488 A1 | 12/2007 | Carr |
| 2008/0015571 A1 | 1/2008 | Rubinsky et al. |
| 2008/0033417 A1 | 2/2008 | Nields et al. |
| 2008/0033418 A1 | 2/2008 | Nields et al. |
| 2008/0033419 A1 | 2/2008 | Nields et al. |
| 2008/0033420 A1 | 2/2008 | Nields et al. |
| 2008/0033422 A1 | 2/2008 | Turner et al. |
| 2008/0058793 A1 | 3/2008 | Pilla et al. |
| 2008/0061055 A1 | 3/2008 | Moriya et al. |
| 2008/0065059 A1 | 3/2008 | Lukowiak et al. |
| 2008/0082093 A1 | 4/2008 | Prakash et al. |
| 2008/0097558 A1 | 4/2008 | Eggers et al. |
| 2008/0097559 A1 | 4/2008 | Eggers et al. |
| 2008/0108985 A1 | 5/2008 | Konesky |
| 2008/0140062 A1 | 6/2008 | Cronin |
| 2008/0147056 A1 | 6/2008 | van der Weide et al. |
| 2008/0149623 A1 | 6/2008 | Givens |
| 2008/0183165 A1 | 7/2008 | Buysse et al. |
| 2008/0183251 A1 | 7/2008 | Azar et al. |
| 2008/0200969 A1 | 8/2008 | Weber |
| 2008/0221650 A1 | 9/2008 | Turner et al. |
| 2008/0228062 A1 | 9/2008 | Zwirn et al. |
| 2008/0234574 A1 | 9/2008 | Hancock et al. |
| 2008/0249530 A1 | 10/2008 | Truckai et al. |
| 2008/0255570 A1 | 10/2008 | Truckai et al. |
| 2008/0255571 A1 | 10/2008 | Truckai et al. |
| 2008/0269851 A1 | 10/2008 | Deem et al. |
| 2008/0275436 A1 | 11/2008 | Cronin et al. |
| 2008/0294155 A1 | 11/2008 | Cronin |
| 2008/0312651 A1 | 12/2008 | Pope et al. |
| 2008/0319437 A1 | 12/2008 | Turner et al. |
| 2009/0024054 A1* | 1/2009 | Lazarus ............... A61B 5/0031 600/549 |
| 2009/0030312 A1 | 1/2009 | Hadjicostis |
| 2009/0054884 A1 | 2/2009 | Farley et al. |
| 2009/0187177 A1* | 7/2009 | Epstein ................. A61B 18/16 606/33 |
| 2009/0248006 A1 | 10/2009 | Paulus et al. |
| 2009/0248007 A1* | 10/2009 | Falkenstein ........... A61B 90/90 606/33 |
| 2010/0016850 A1* | 1/2010 | Ron Edoute ........... A61N 1/328 606/41 |

FOREIGN PATENT DOCUMENTS

| | | |
|---|---|---|
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10328514 B3 | 3/2005 |
| DE | 102004022206 A1 | 12/2005 |
| DE | 202005015147 U1 | 2/2006 |
| EP | 0 246 350 A1 | 11/1987 |
| EP | 0519415 A1 | 12/1992 |
| EP | 0 521 264 A2 | 1/1993 |
| EP | 0 556 705 A1 | 8/1993 |
| EP | 0 558 429 A1 | 9/1993 |
| EP | 694291 A1 | 1/1996 |
| EP | 0 836 868 A2 | 4/1998 |
| EP | 0 882 955 A1 | 12/1998 |
| EP | 1 159 926 A2 | 12/2001 |
| EP | 1645236 A1 | 4/2006 |
| EP | 1 810 627 A1 | 7/2007 |
| FR | 179 607 | 11/1906 |
| FR | 1 275 415 A | 11/1961 |

(56) References Cited

FOREIGN PATENT DOCUMENTS

| | | |
|---|---|---|
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 5-5106 | 1/1993 |
| JP | 05-40112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09010223 A | 1/1997 |
| JP | 11244298 A | 9/1999 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001128990 A | 5/2001 |
| JP | 2008142467 A | 6/2008 |
| SU | 166452 | 11/1964 |
| SU | 401367 | 10/1973 |
| SU | 727201 A2 | 4/1980 |
| WO | 0054682 A1 | 9/2000 |

OTHER PUBLICATIONS

European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
U.S. Appl. No. 08/483,742, filed Jun. 7, 1995.
U.S. Appl. No. 08/136,098, filed Oct. 14, 1993.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/251,857, filed Oct. 15, 2008.
U.S. Appl. No. 12/253,457, filed Oct. 17, 2008.
U.S. Appl. No. 12/389,906, filed Feb. 20, 2009.
U.S. Appl. No. 12/389,915, filed Feb. 20, 2009.
U.S. Appl. No. 12/401,268, filed Mar. 10, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
U.S. Appl. No. 12/487,917, filed Jun. 19, 2009.
U.S. Appl. No. 12/493,302, filed Jun. 29, 2009.
U.S. Appl. No. 12/504,738, filed Jul. 17, 2009.
U.S. Appl. No. 12/535,851, filed Aug. 5, 2009.
U.S. Appl. No. 12/535,856, filed Aug. 5, 2009.
U.S. Appl. No. 12/536,616, filed Aug. 6, 2009.
U.S. Appl. No. 12/542,348, filed Aug. 17, 2009.
U.S. Appl. No. 12/542,785, filed Aug. 18, 2009.
U.S. Appl. No. 12/547,155, filed Aug. 25, 2009.
U.S. Appl. No. 12/548,644, filed Aug. 27, 2009.
U.S. Appl. No. 12/555,576, filed Sep. 8, 2009.
U.S. Appl. No. 12/556,010, filed Sep. 9, 2009.
U.S. Appl. No. 12/561,096, filed Sep. 16, 2009.
U.S. Appl. No. 12/562,575, filed Sep. 18, 2009.
U.S. Appl. No. 12/562,842, filed Sep. 18, 2009.
U.S. Appl. No. 12/566,299, filed Sep. 24, 2009.
U.S. Appl. No. 12/568,067, filed Sep. 28, 2009.
U.S. Appl. No. 12/568,524, filed Sep. 28, 2009.
U.S. Appl. No. 12/568,551, filed Sep. 28, 2009.
U.S. Appl. No. 12/568,777, filed Sep. 29, 2009.
U.S. Appl. No. 12/568,838, filed Sep. 29, 2009.
U.S. Appl. No. 12/568,883, filed Sep. 29, 2009.
U.S. Appl. No. 12/568,972, filed Sep. 29, 2009.
U.S. Appl. No. 12/569,171, filed Sep. 29, 2009.
U.S. Appl. No. 12/569,685, filed Sep. 29, 2009.
U.S. Appl. No. 12/582,857, filed Oct. 21, 2009.
U.S. Appl. No. 12/606,769, filed Oct. 27, 2009.
U.S. Appl. No. 12/607,221, filed Oct. 28, 2009.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.

(56) References Cited

OTHER PUBLICATIONS

Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTech product literature (Dec. 1999) "FlexStrand": product description, 1 page.
MDTech product literature (Mar. 2000) I'D Wire: product description, 1 page.
Medtrex Brochure "The O.R. Pro 300" 1 page, Sep. 1998.
Michael Choti, "Abdominoperineal Resection with the LigaSure.TM. Vessel Sealing System and LigaSure.TM. Atlas 20 cm Open Instrument" Innovations That Work, Jun. 2003.
Muller et al., "Extended Left Hemicolectomy Using the LigaSure.TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . ." Journal of Applied Sciences Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.

Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Christopher L. Brace, "Temperature-Dependent Dielectric Properties of Liver Tissue Measured During Thermal Ablation: Toward an Improved Numerical Model" 2008 IEEE pp. 230-233.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 03721482 dated Feb. 6, 2006.
European Search Report EP 04009964 dated Jul. 28, 2004.
U.S. Appl. No. 12/607,268, filed Oct. 28, 2009.
U.S. Appl. No. 12/619,462, filed Nov. 16, 2009.
U.S. Appl. No. 12/620,289, filed Nov. 17, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.

(56) References Cited

OTHER PUBLICATIONS

B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Dumey et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 In Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. Mi, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure.TM. Vessel Sealing System: A Case Report" Innovations That Work, Feb. 2002.
Humphries Jr. et al., "Finite-Element Codes to Model Electrical Heating and Non-L1near Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure.TM. Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure.TM. Vessel Sealing System in Hemorrhoidectormy" American College of Surgeons (ACS) Clinic La Congress Poster (2000).
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09166708 dated Oct. 15, 2009.
European Search Report EP 09169376.2 extended dated Dec. 16, 2009.
European Search Report EP 09172838.6 extended dated Jan. 20, 2010.
European Search Report EP 09173268.5 extended dated Jan. 27, 2010.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.
Esterline, "Light Key Projection Keyboard" Advanced Input Systems, located at: <http://www.advanced-input.com/lightkey> 2002.
Urologix, Inc.—Medical Professionals: Targis.TM. Technology. "Overcoming the Challenge" located at: <http://www.urologix.com!medicaUtechnology.html > Nov. 18, 1999; 3 pages.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.

(56) References Cited

OTHER PUBLICATIONS

European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.

* cited by examiner

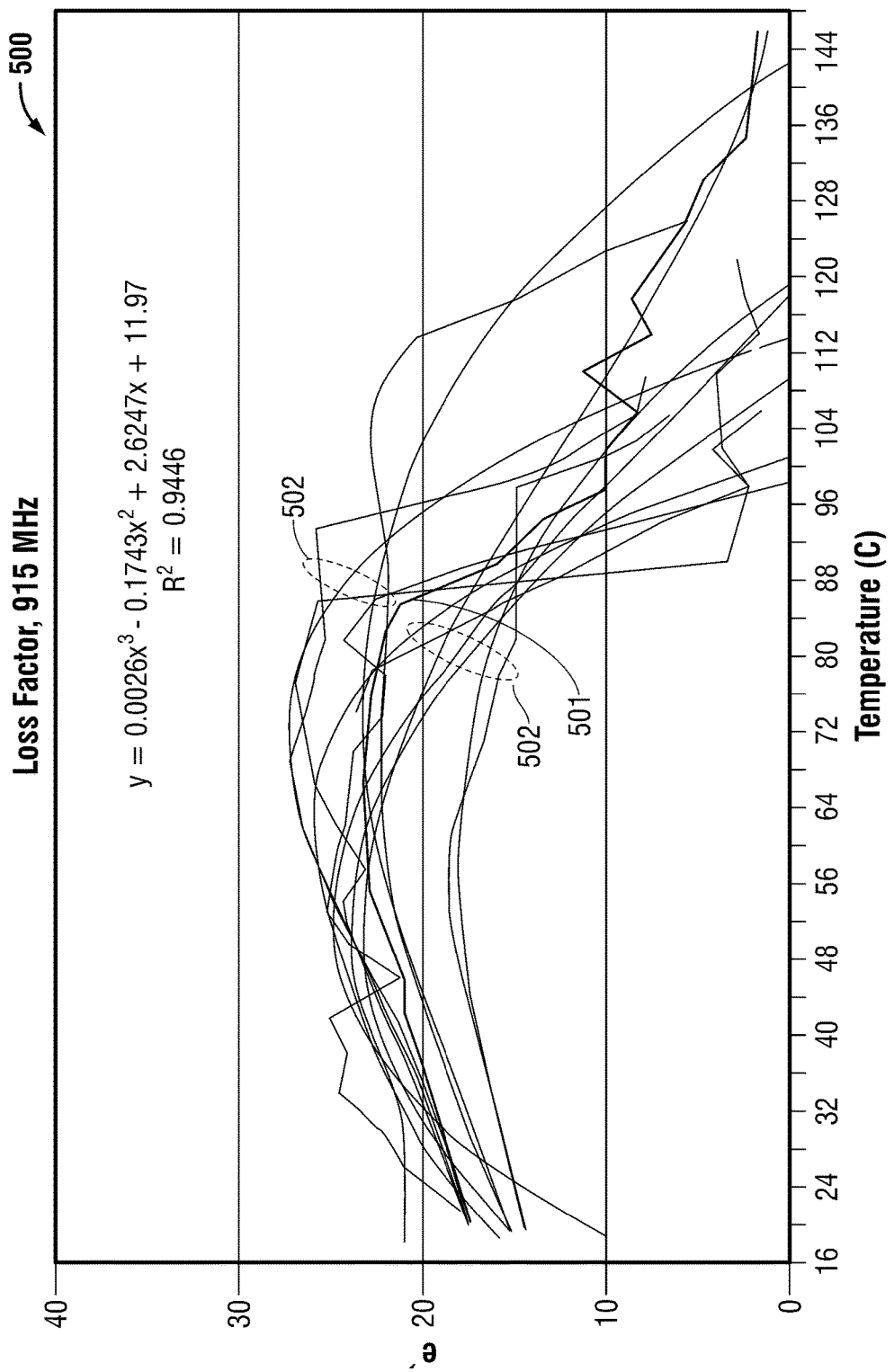

MICROWAVE ABLATION SYSTEM WITH DIELECTRIC TEMPERATURE PROBE

REFERENCE TO RELATED APPLICATIONS

The present application is a continuation application of U.S. patent application Ser. No. 12/642,623, now U.S. Pat. No. 8,882,759, filed on Dec. 18, 2009, the entire contents of which are incorporated by reference herein.

BACKGROUND

1. Technical Field

The present disclosure relates to systems and methods for providing energy to biological tissue and, more particularly, to apparatus and methods for sensing thermal and dielectric parameters of tissue during a microwave ablation procedure.

2. Background of Related Art

There are several types of microwave antenna assemblies in use, e.g., monopole, dipole and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors, which are linearly aligned and positioned end-to-end relative to one another with an electrical insulator placed therebetween. Helical antenna assemblies include a helically-shaped conductor connected to a ground plane. Helical antenna assemblies can operate in a number of modes including normal mode (broadside), in which the field radiated by the helix is maximum in a perpendicular plane to the helix axis, and axial mode (end fire), in which maximum radiation is along the helix axis. The tuning of a helical antenna assembly may be determined, at least in part, by the physical characteristics of the helical antenna element, e.g., the helix diameter, the pitch or distance between coils of the helix, and the position of the helix in relation to the probe assembly to which it is mounted.

The typical microwave antenna has a long, thin inner conductor that extends along the longitudinal axis of the probe and is surrounded by a dielectric material and is further surrounded by an outer conductor around the dielectric material such that the outer conductor also extends along the axis of the probe. In another variation of the probe that provides for effective outward radiation of energy or heating, a portion or portions of the outer conductor can be selectively removed. This type of construction is typically referred to as a "leaky waveguide" or "leaky coaxial" antenna. Another variation on the microwave probe involves having the tip formed in a uniform spiral pattern, such as a helix, to provide the necessary configuration for effective radiation. This variation can be used to direct energy in a particular direction, e.g., perpendicular to the axis, in a forward direction (i.e., towards the distal end of the antenna), or combinations thereof.

Invasive procedures and devices have been developed in which a microwave antenna probe may be either inserted directly into a point of treatment via a normal body orifice or percutaneously inserted. Such invasive procedures and devices potentially provide better temperature control of the tissue being treated. Because of the small difference between the temperature required for denaturing malignant cells and the temperature injurious to healthy cells, a known heating pattern and predictable temperature control is important so that heating is confined to the tissue to be treated. For instance, hyperthermia treatment at the threshold temperature of about 41.5° C. generally has little effect on most malignant growth of cells. However, at slightly elevated temperatures above the approximate range of 43° C. to 45° C., thermal damage to most types of normal cells is routinely observed. Accordingly, great care must be taken not to exceed these temperatures in healthy tissue.

In the case of tissue ablation, a high radio frequency electrical current in the range of about 500 MHz to about 10 GHz is applied to a targeted tissue site to create an ablation volume, which may have a particular size and shape. Ablation volume is correlated to antenna design, antenna tuning, antenna impedance and tissue impedance. Tissue impedance may change during an ablation procedure due to a number of factors, e.g., tissue denaturization or desiccation occurring from the absorption of microwave energy by tissue. Changes in tissue impedance may cause an impedance mismatch between the probe and tissue, which may affect delivery of microwave ablation energy to targeted tissue. The temperature and/or impedance of targeted tissue, and of non-targeted tissue and adjacent anatomical structures, may change at a varying rates which may be greater, or less than, expected rates. A surgeon may need to perform an ablation procedure in an incremental fashion in order to avoid exposing targeted tissue and/or adjacent tissue to excessive temperatures and/or denaturation. In certain circumstances, a surgeon may need to rely on experience and/or published ablation probe parameters to determine an appropriate ablation protocol (e.g., ablation time, ablation power level, and the like) for a particular patient.

SUMMARY

The present disclosure is directed to an electromagnetic surgical ablation system that includes a tissue sensor probe that is adapted to sense tissue temperature and/or tissue impedance at or near an ablation surgical site. The disclosed tissue sensor probe may include an absorbent coating or sleeve that is configured to control and/or absorb condensation that may form on a sensing probe shaft, which, if left unchecked, may impair the accuracy of the sensor. Also disclosed is a control module which may include a database configured to predict ablation characteristics over the duration of an ablation procedure. In embodiments, the database includes parameters related to any of dielectric properties, impedance properties, and thermal properties. A lookup table may be included which relates temperature-related parameters to dielectric-related parameters, e.g., relative permittivity (e') and/or relative loss factor (e") over an ablation frequency range of about 500 MHz to about 10 GHz. In an embodiment, the lookup table relates temperature-related parameters to relative permittivity (e') and relative loss factor (e") at an operating frequency of about 915 MHz and about 2.45 GHz.

Relative permittivity, sometimes referred to as the dielectric constant, is a measure of how an electric field affects, and is affected by, a dielectric medium. Relative permittivity relates to the ability of a material to polarize in response to the field to reduce the total electric field inside the material, and thus relates to a material's ability to transmit (or "permit") an electric field. The force (F) between two electric charges (e) at a distance (d) apart in a vacuum is expressed as $F = e^2/d^2$. In any other medium, e.g., air or tissue, the force is expressed as $F = e^2/e'_r d^2$ where e' is the relative permittivity (dielectric constant) of the dielectric medium. Typical relative permittivity values include, e.g., 1.0 for air, 1.013 for steam; 80.36 for water at 20° C. Relative permittivity is temperature and frequency dependent.

Dielectric loss factor (e″), sometimes referred to as to conductivity, is related to relative permittivity. Loss factor e″ is a measure of the loss of energy in a dielectric material through, e.g., conduction, slow polarization currents, and other dissipative phenomena. The peak value for a dielectric with no direct-current conductivity occurs at the relaxation frequency, which is temperature related. The maximum value can be used as a measure of the dielectric properties of tissue.

The disclosed surgical ablation system may include a source of microwave ablation energy, such as generator, that is responsive to a control signal generated by the control module. The tissue sensor probe and generator function cooperatively to enable a surgeon to monitor temperature and/or impedance at, or adjacent to, an ablation surgical site.

In one aspect, the disclosed use of a dielectric sensor in combination with a temperature sensor provides benefits which exceed those which accrue from the use of a dielectric or a temperature sensor alone. For example, and without limitation, the use of dielectric data and temperature data together enables the system to more accurately differentiate between desiccated ("charred") tissue, and non-tissue substances such as air, which can co-exist at similar temperatures at an operative site.

In addition, the present disclosure provides an electromagnetic surgical ablation system having a generator adapted to selectively provide surgical ablation energy to an ablation probe. The ablation probe is operably coupled to the generator and adapted to receive ablation energy therefrom, and to deliver said ablation energy to targeted tissue, e.g., a tumor, polyp, or necrotic lesion. The disclosed system includes a controller operatively coupled to the generator, the controller including at least one processor, a memory operatively coupled to the processor, a dielectric sensor circuit operatively coupled to the processor and adapted to receive a dielectric sensor signal from a tissue sensor probe, and a temperature sensor circuit operatively coupled to the processor and adapted to receive a temperature sensor signal from a tissue sensor probe. The electromagnetic surgical ablation system also includes a tissue sensor probe operatively coupled to the controller. The tissue sensor probe includes a dielectric sensor disposed at a distal end thereof configured to provide a dielectric sensor signal corresponding to a dielectric property of tissue. The tissue sensor probe further includes a temperature sensor disposed at a distal end thereof configured to provide a temperature sensor signal corresponding to a temperature of tissue.

Also disclosed is a method of operating an electromagnetic surgical ablation system. The disclosed method includes the steps of activating a source of electromagnetic surgical energy, sensing a tissue temperature, deactivating the source of electromagnetic surgical energy upon expiration of a predetermined period of time, a sensing at least one tissue dielectric property, e.g., a permittivity and/or a loss factor, determining a tissue status from at least one of the sensed tissue temperature and the at least one sensed tissue dielectric property, and activating the source of electromagnetic surgical energy in response to a determination that the tissue is not sufficiently ablated.

The present disclosure also provides a computer-readable medium storing a set of programmable instructions configured for being executed by at least one processor for performing a method of performing microwave tissue ablation in response to monitored tissue temperature and/or monitored tissue dielectric properties in accordance with the present disclosure.

BRIEF DESCRIPTION OF THE DRAWINGS

The above and other aspects, features, and advantages of the present disclosure will become more apparent in light of the following detailed description when taken in conjunction with the accompanying drawings in which:

FIG. 7A illustrates a relationship between loss factor and temperature at an ablation frequency of 915 MHz in accordance with an embodiment of the present disclosure.

DETAILED DESCRIPTION

Figure 1:
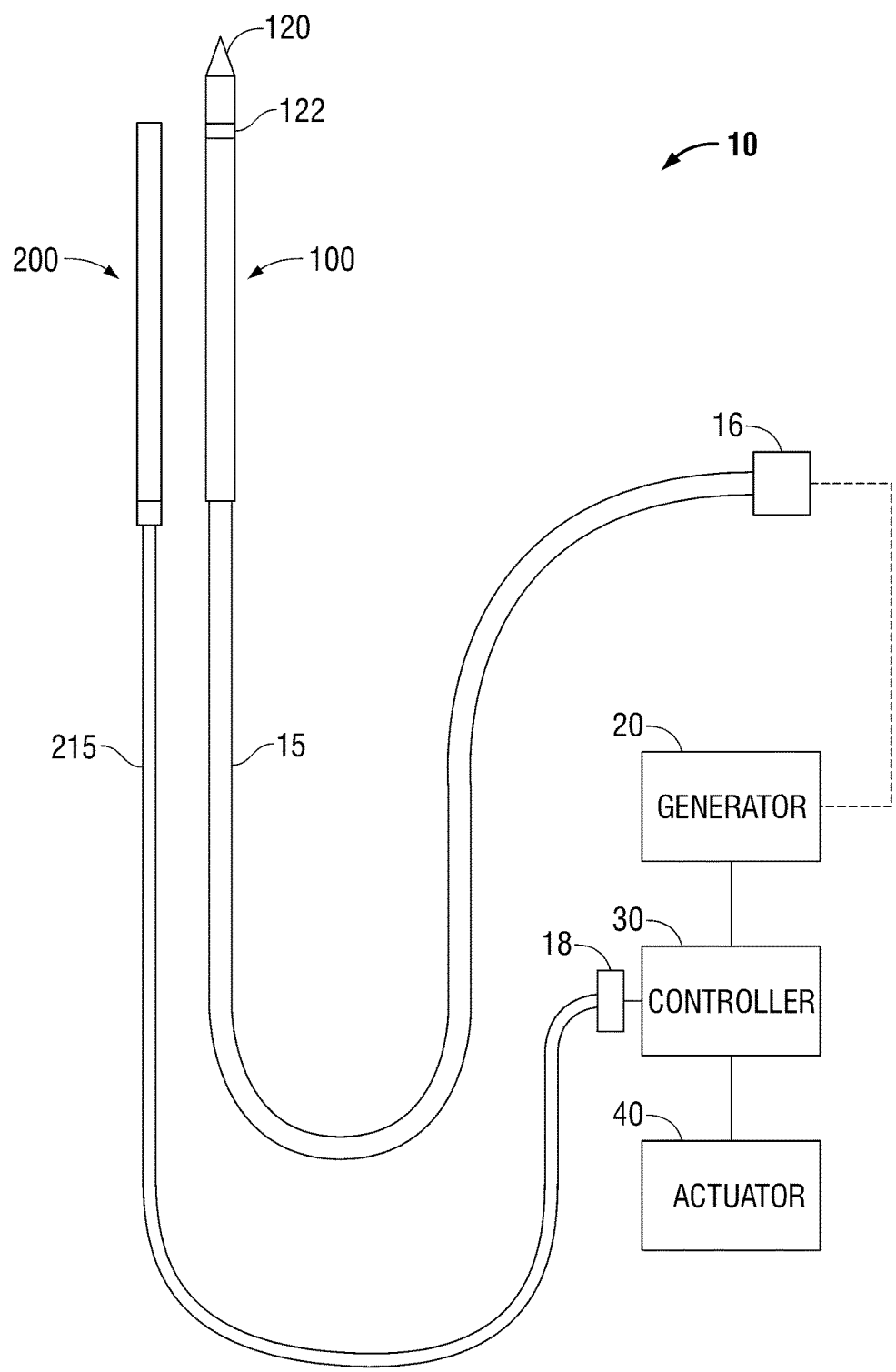
FIG. 1 shows a diagram of a microwave ablation system having an electromagnetic surgical ablation probe and a tissue sensor probe in accordance with an embodiment of the present disclosure.

Particular embodiments of the present disclosure will be described hereinbelow with reference to the accompanying drawings; however, it is to be understood that the disclosed embodiments are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, shall refer to the end of the instrument that is closer to the user, while the term "distal" shall refer to the end that is farther from the user.

FIG. 1 shows an embodiment of a microwave ablation system 10 in accordance with the present disclosure. The microwave ablation system 10 includes an electromagnetic surgical ablation probe 100 having a tapered distal tip 120 and a feed point 122. The ablation probe 100 is operably connected by a cable 15 to connector 16, which may further operably connect probe 100 to a generator assembly 20. Generator assembly 20 may be a source of ablation energy, e.g., microwave or RF energy in the range of about 915 MHz to about 2.45 GHz. The disclosed system 10 includes a tissue sensor probe 200 that is adapted to sense at least one operative parameter, e.g., a tissue temperature and/or a tissue dielectric parameter, e.g., a relative permittivity, a dielectric constant, a dielectric loss factor and/or a conductivity. The tissue sensor probe 200 is operably connected by a cable 215 to connector 18, which may further operably connect tissue sensor probe 200 to a controller assembly 30. An actuator 40 is operably coupled to the controller to enable a user, e.g., a surgeon, to selectively activate and de-activate the delivery of ablation energy to patient tissue. Controller 30 is operably coupled to generator 20 to enable communication therebetween, such as without limitation, a control signal and/or a status signal.

Figure 2:
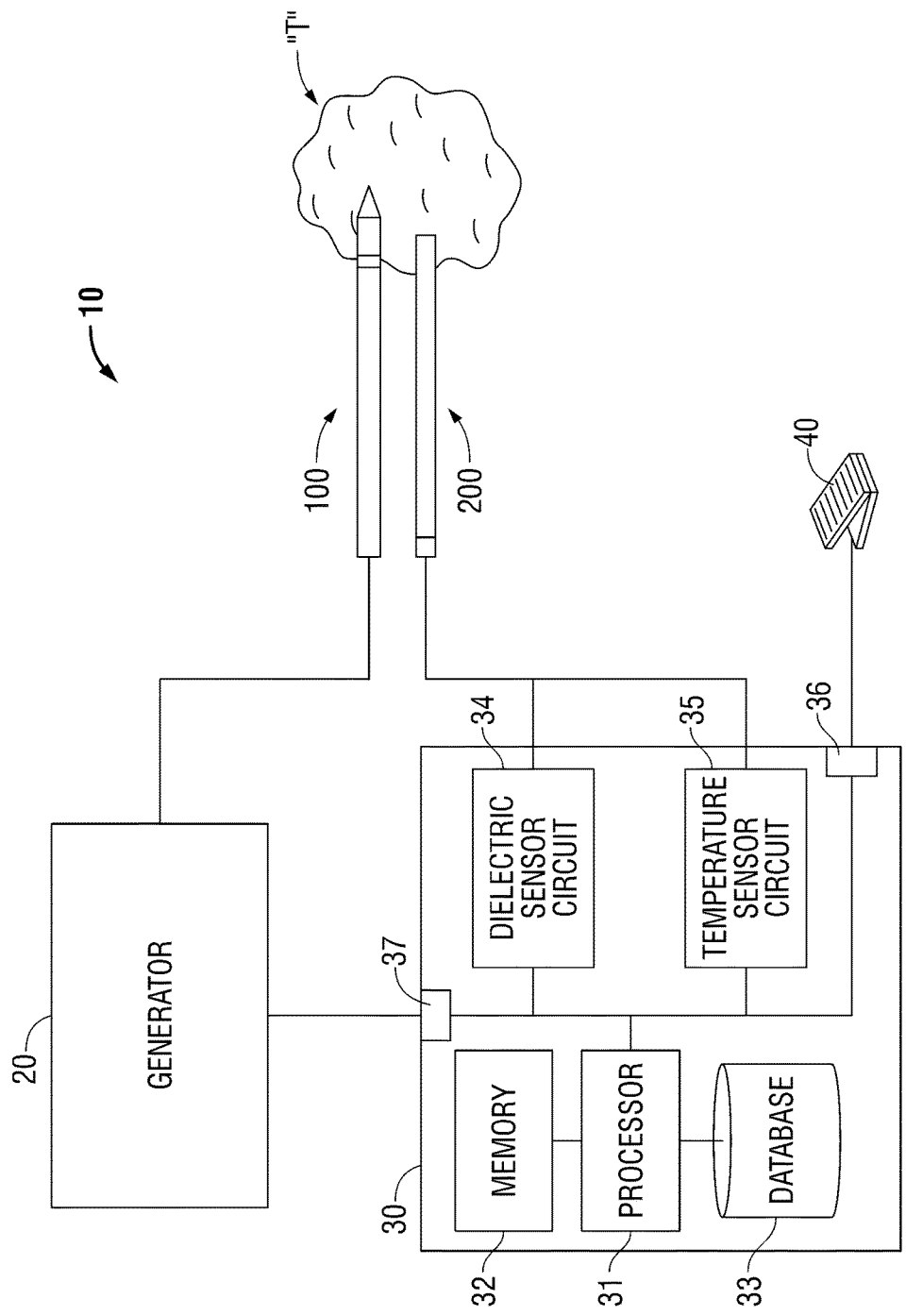
FIG. 2 shows a block diagram of a microwave ablation system having an electromagnetic surgical ablation probe and a tissue sensor probe in accordance with an embodiment of the present disclosure.

In more detail, FIG. 2 illustrates a functional block diagram of an ablation system 10 in accordance with the present disclosure. The system 10 includes a controller 30 that includes one or more processors 31 operatively coupled to memory 32, database 33, dielectric sensor circuit 34, and temperature sensor circuit 35. Processor(s) 31 may be configured to execute a set of programmed instructions for performing a method of microwave ablation as disclosed herein. Controller 30 includes actuator interface 36 that is adapted to facilitate operative coupling with actuator 40 and/or a generator interface 37 that is adapted to facilitate operative coupling with generator 20. Actuator 40 may be any suitable actuator, such as without limitation, a footswitch, a handswitch (which may be mounted on a probe 100 and/or a tissue sensor probe 200), an orally-activated switch (e.g., a bite-activated switch and/or a breath-actuated switch), and the like. The processor(s) 31, memory 32, database 33, dielectric sensor circuit 34, temperature sensor circuit 35, actuator interface 36 and/or generator interface 37 may be separate components or may be integrated, such as in one or more integrated circuits. The various components in the controller 30 may be coupled by one or more communication buses or signal lines 38. Memory 30 and/or database 33 may include a set of executable instructions for performing a method of microwave ablation as described herein. One or more elements of ablation system 10 may be coupled using hard-wired connections and/or a wireless link. During use, tissue sensor probe 200 may be positioned in tissue T in proximity to probe 100 to obtain at least one tissue parameter.

Figure 3:
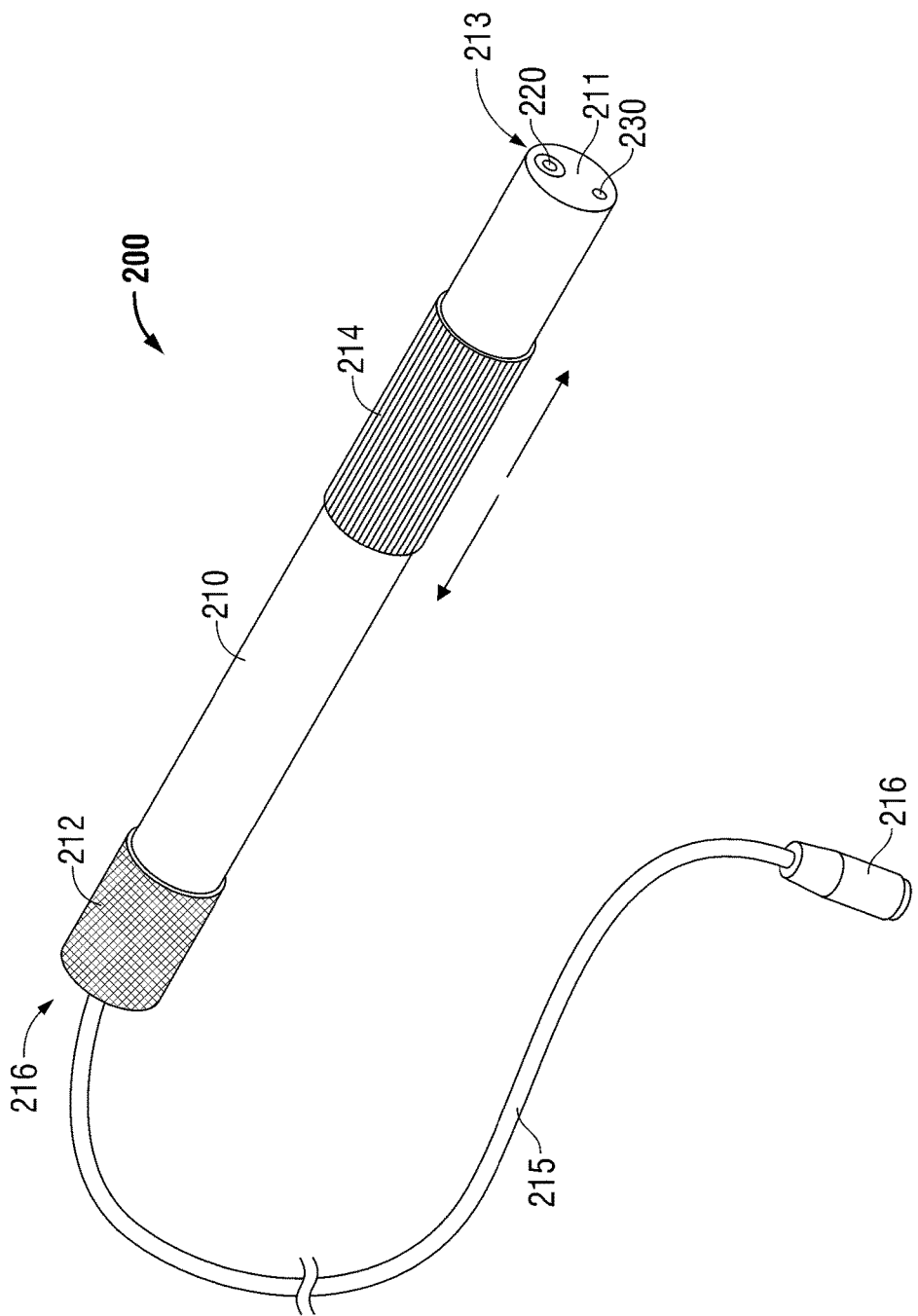
FIG. 3 is a perspective view of a tissue sensor probe in accordance with an embodiment of the present disclosure.
Figure 4:
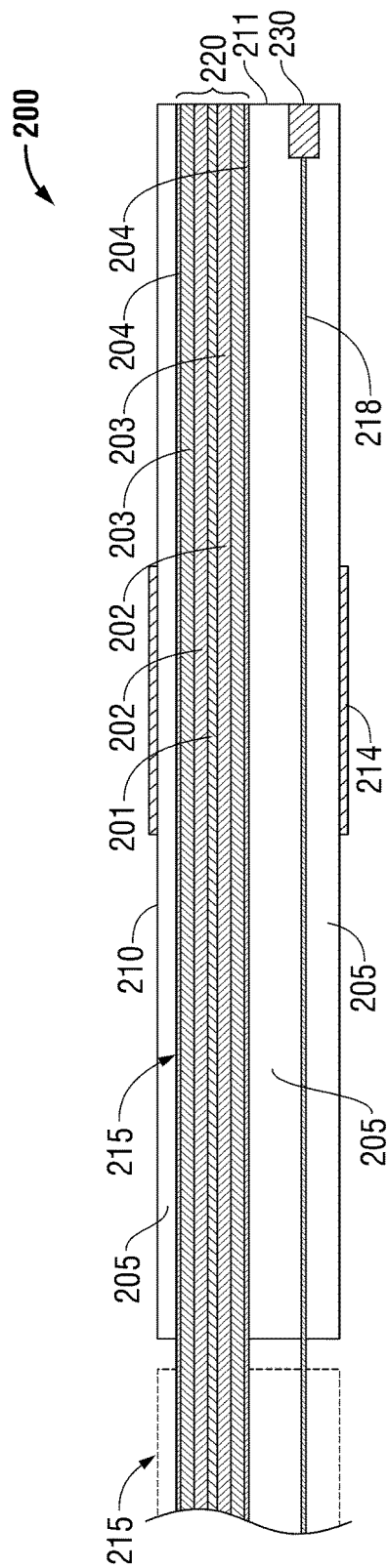
FIG. 4 is a side, cross-sectional view of a tissue sensor probe in accordance with an embodiment of the present disclosure.

An embodiment of a tissue sensor probe 200 in accordance with the present disclosure is now described with reference to FIGS. 3 and 4. Probe 200 includes an elongated generally cylindrical shaft 210 having a distal end 213 and a proximal end 216. Dielectric sensor 220 and/or temperature sensor 230 is disposed on a distal surface 211 of sensor shaft 210 to facilitate the measurement of at least one tissue parameter when probe 200 is in contact with tissue. The probe 200 includes one or more absorbent sleeves 214 disposed on the shaft 210 and adapted to attract and absorb moisture, e.g., steam and/or condensed water vapor, which may be released as a byproduct of an ablation procedure and collect on the probe shaft 210. In envisioned embodiments, absorbent sleeve(s) 214 may be slidably disposed on shaft 210 to enable the selective absorption of moisture, and/or to enable a surgeon to position sleeve 214 according to surgical requirements. Sleeve(s) 214 may be formed from any suitable biocompatible absorbent material, including without limitation paper-based material composed of virgin wood pulp that is obtained from certified forests.

Probe 200 includes a handle 212 positioned at a proximal end 216 of the probe 200. Handle 212 may include grip-enhancing features such as, without limitation, knurling, ridges, coatings (e.g., silicone-based or rubberized coating) disposed on at least a part of an outer surface of the handle 212. Probe 200 includes a cable 215 extending therefrom that is adapted to operably couple dielectric sensor 220 with dielectric sensor circuit 34, and/or to operably couple temperature sensor 230 with temperature sensor circuit 35. Shaft 210 of tissue sensor 200 may have any suitable length and/or diameter suitable for use in an ablation procedure. In embodiments, shaft 210 may have a length of about 10 cm to about 30 cm.

Dielectric sensor 220 includes a coaxial cable 206 disposed within the shaft 210. Coaxial cable 206 includes an inner conductor 201 coaxially disposed within an insulator 202, which, in turn, is coaxially disposed within an outer conductor 203. An insulating outer sheath 204 is coaxially disposed about outer conductor 203. A distal end 217 of coaxial cable 206 is positioned substantially flush with a distal end 211 of probe 200 and configured such that the inner conductor 201, insulator 202, outer conductor 203, or outer sheath 204 is exposed at a distal end thereof to facilitate contact with tissue. During use, dielectric sensor 220 and dielectric sensor circuit 34 are operatively coupled (by, e.g., coaxial cable 206 and/or cable 215) to enable controller 30 to determine a dielectric property of tissue, e.g., permittivity and/or loss factor, by any suitable manner of dielectric measurement, such as, without limitation, time domain reflectometry, broadband vector reflectometry, and/or scattering parameter (S-parameter) analysis techniques. In one embodiment, dielectric sensor circuit 34 may generate a microwave test signal that is transmitted through cable 215 and/or coaxial cable 206, to dielectric sensor 220, and to tissue, which, in turn, causes at least a portion of the transmitted test signal to be reflected back to dielectric sensor circuit 34 as a reflected test signal. Dielectric sensor circuit 34 is configured to detect an electrical property of the reflected test signal, e.g., a phase, an amplitude, and/or a frequency, and determine a dielectric tissue property therefrom, e.g., a permittivity and/or a loss factor. Dielectric sensor circuit 34 may perform a comparison between phase, amplitude, and/or frequency properties of a transmitted test signal and a reflected test signal.

Tissue sensor probe 200 includes a temperature sensor 230 disposed at a distal end 211 of the probe shaft 210. Temperature sensor 230 may include any suitable temperature-sensing transducer, including without limitation, a fluoroptic (e.g., fiber optic) sensor, a thermocouple, a thermistor, an infrared thermometer (e.g., emissive measurement), or other temperature sensor now or in the future known. Temperature sensor 230 is operatively coupled to temperature sensor circuit 35 via connection element 218, which may include electrical and/or fiber optic conductors. Temperature sensor circuit 35 is adapted to receive a temperature measurement signal from temperature sensor 230 to determine a tissue temperature, which, in turn, may be utilized by controller 30 and/or generator 20.

Since power levels required for ablation may exceed that required of a transmitted test signal and/or exhibited by a reflected test signal, the ablation signal may overload dielectric sensor circuit 34 or otherwise cause erroneous results. To reduce or eliminate the likelihood of interference between an ablation signal and a test signal, attention is directed to FIG. 5 which illustrates a method 300 for operating a microwave ablation system 10 wherein the system 10 includes a generator 20, controller 30, ablation probe 100, and tissue sensor probe 200.

The disclosed method begins in the step 301 wherein one or more initializations may be performed, e.g., power-on self test (POST), memory allocation, input/output (I/O) initialization, and the like. In the step 305 it is determined whether an activation signal is present, e.g., whether actuator 40 has been engaged by a user to cause delivery of ablation energy to tissue. If no activation signal is present, the process iterates until an activation signal is detected (e.g., the system enters a "wait state"). Upon receipt of an activation signal, the process continues with the step 310 wherein a cycle timer is initialized. The cycle timer may be a software or hardware-driven clock that is adapted to observe the time interval between measurements. During an ablation procedure, the ablation signal may periodically be interrupted upon expiration of a cycle time to enable a test signal to be applied to tissue to obtain a dielectric measurement. Because the ablation signal is suspended during the measurement window, a measurement may be obtained without interference from the ablation signal. A cycle time may range from about 10 msec to about 10 seconds. In an embodiment, cycle time may be about one second (e.g., a dielectric measurement is taken about once per second).

Having reset the cycle time, the procedure continues with the step 315 wherein an ablation generator, e.g., generator 20, is activated to deliver ablation energy to tissue via an ablation probe 100. In an embodiment, in the step 315 an ablation control signal may be generated by controller 30 and conveyed to ablation generator 20 via generator interface 37. In the step 320, a tissue temperature measurement T is obtained. In an embodiment, tissue temperature measurement T is obtained from temperature sensor 230 of tissue sensor probe 200. In the step 325, the cycle timer is evaluated to determine whether the cycle time has expired, e.g., whether it is time to perform a dielectric measurement. If the cycle timer has not expired, the step 330 is performed wherein a determination is made whether the activation signal is still present, e.g., the user is indicating by continued engagement of the actuator 40 that the ablation procedure is to proceed. If it is determined the activation signal is no longer present, the process concludes with the step 360. In an alternative embodiment, if in the step 330 it is determined the activation signal is no longer present, the process may iterate to the step 305 wherein a wait loop is entered.

Figure 5:
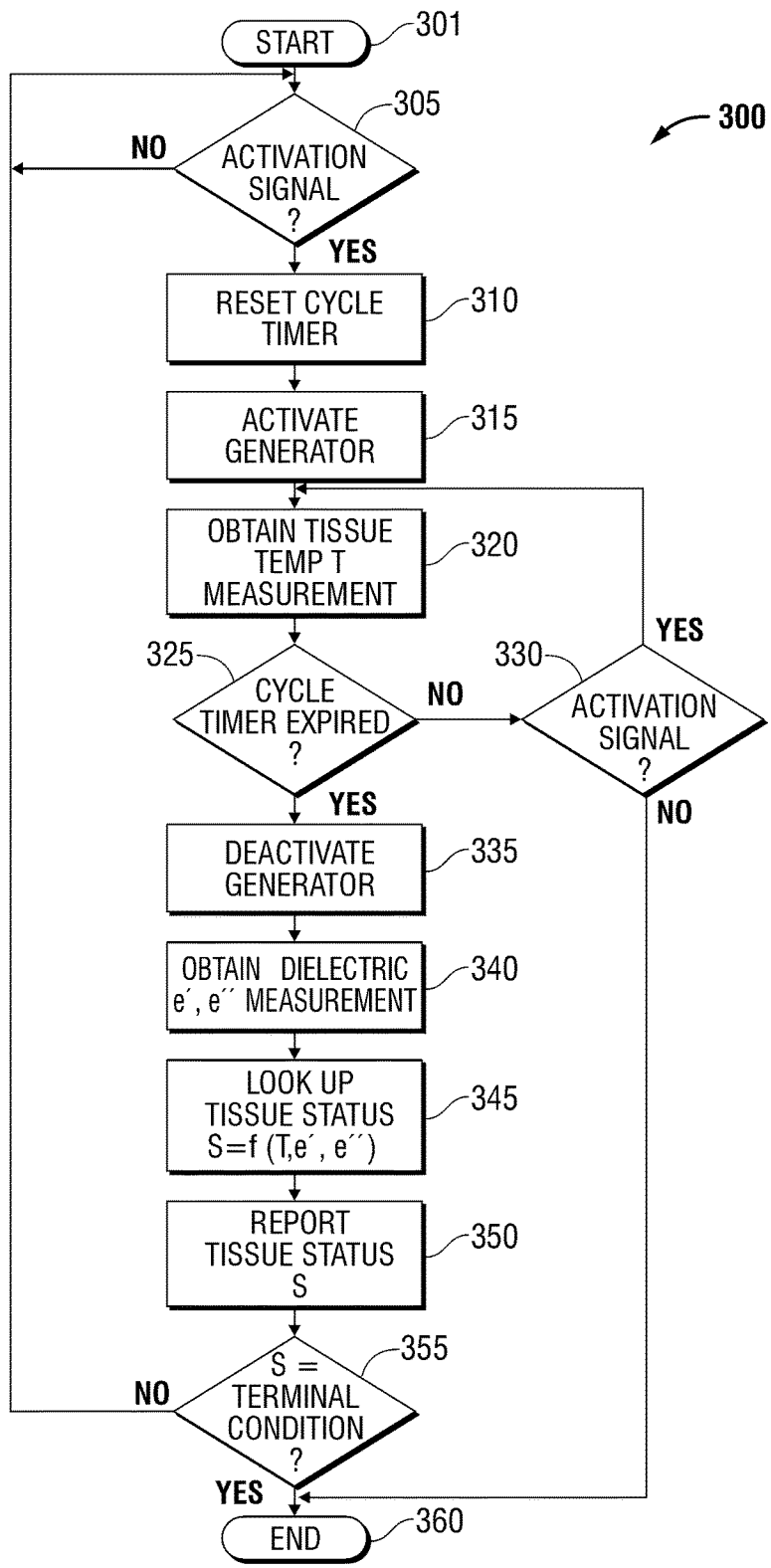
FIG. 5 is a flowchart showing a method of operation of microwave ablation system having a tissue sensing probe in accordance with an embodiment of the present disclosure.

If, in the step 325, it is determined the cycle time is expired, the step 335 is performed wherein the ablation generator is deactivated, thereby enabling at least one tissue dielectric measurement to be performed in the step 340. In an embodiment, a time delay or pause may be observed between the deactivation step 335 and the dielectric measurement step 340, which may improve or enhance the accuracy of the dielectric measurement. As shown in FIG. 5, a permittivity (e') and/or a loss factor (e") dielectric measurement may be performed, however, it in envisioned that one or more additional or alternative measurements may be performed in the step 340.

In step 345, a tissue temperature measurement, a tissue permittivity measurement e', and a tissue loss factor e" are utilized to determine a tissue status S. Tissue status S may be indicative of whether the sensed tissue has received insufficient, sufficient, and/or excessive ablation energy, e.g., whether the tissue is underablated ("undercooked"), ablated ("cooked"), or hyper-ablated ("charred"). Other tissue statuses are envisioned, for example without limitation a near-ablated ("pre-cooked") status. In one embodiment, a lookup table (not explicitly shown) may be utilized to ascertain tissue status based upon on temperature, permittivity, and loss factor. A lookup table in accordance with the present disclosure may have a three-dimensional organization whereby a first table dimension is representative of tissue temperature, a second table dimension is representative of tissue permittivity, and a third table dimension is representative of tissue loss factor. In this manner, each of temperature, permittivity, and loss factor are thus utilized as indices into the three dimensional table to identify a particular tissue status corresponding thereto. In an embodiment, a lookup table may be included within database 33.

In step 350, a tissue status signal may be reported to a user via any suitable manner of communication, such as without limitation, an audible signal, a visual signal, a haptic (tactile) signal, and/or a combination thereof. By way of example only, an underablated status may be excluded from reporting, since this is routinely observed and expected during an initial phase of an ablation procedure. As tissue approaches ablated status, e.g., attains near-ablated status, a first tissue status signal, e.g., a short audible signal, may be issued to apprise a user accordingly. When tissue reaches ablated status, a second tissue status signal may be issued, e.g., a more urgent audible signal, alone or in combination with a visual signal. In embodiment, multiple tissue statuses may be utilized to convey a continuous indication of ablation progress. In this manner, a user may be assisted in the accurate and timely assessment of ablation progress, in real-time, during an ablation procedure.

A tissue status may be associated with a terminal condition whereby attainment of a terminal status indicates that the ablation procedure is complete and/or that delivery of ablation is to be terminated. In the step 355, a determination is made whether the currently-identified tissue status is a terminal status. If the current tissue status is not a terminal status, the process iterates with the step 305 whereupon presence of an activation signal is confirmed, and the ablation procedure continues as just described. Conversely, if a terminal status is reached, the ablation process concludes with the step 360.

It is to be understood that the steps of the method provided herein may be performed in combination and/or in a different order than presented herein without departing from the scope and spirit of the present disclosure.

Figure 6A:
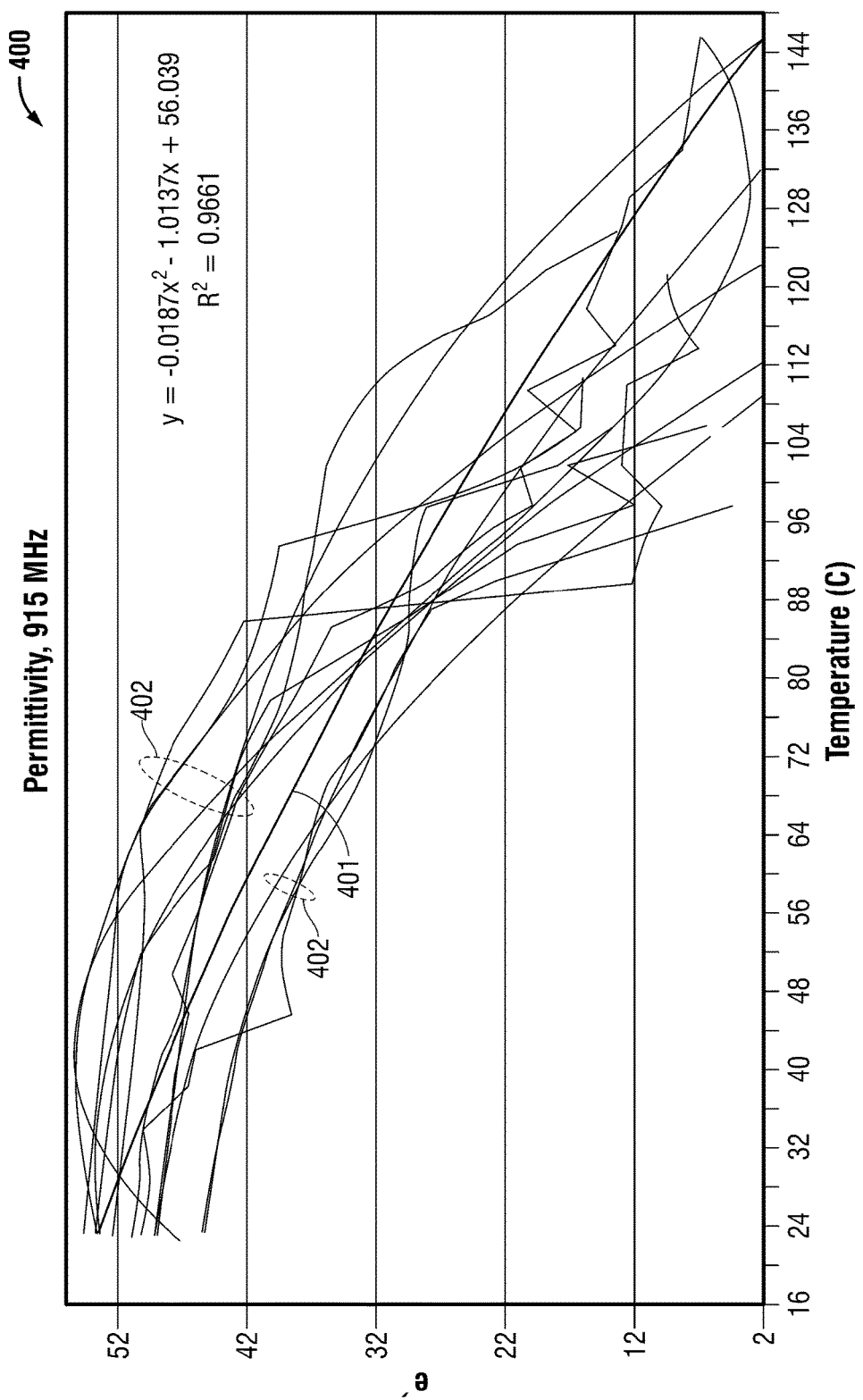
FIG. 6A illustrates a relationship between permittivity and temperature at an ablation frequency of 915 MHz in accordance with an embodiment of the present disclosure.
Figure 6B:
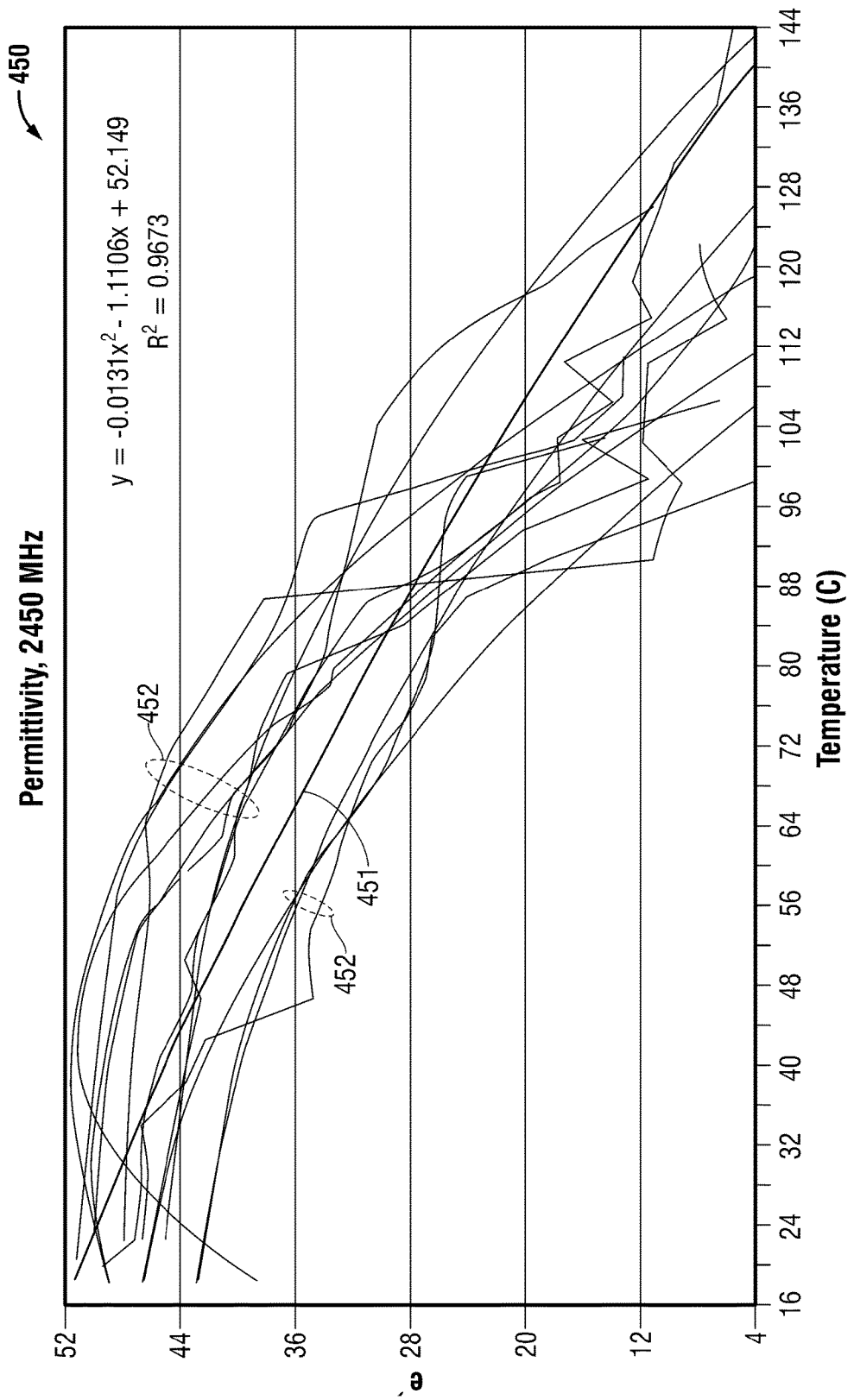
FIG. 6B illustrates a relationship between permittivity and temperature at an ablation frequency of 2.45 GHz in accordance with an embodiment of the present disclosure.

Relationships between tissue permittivity and tissue temperature are illustrated in FIG. 6A, which depicts the relationships at an ablation frequency of 915 MHz, and FIG. 6B, which depicts the relationships at an ablation frequency of 2.45 GHz. As shown in FIG. 6A, a series of test ablations yields a set of trend lines 402. The inventors have determined that an average 401 of trend lines 402 may be expressed as a quadratic relationship $y=-0.0185x^2-1.0137x+56.039$, which yields a coefficient of determination (e.g., $R^2$) of about 0.9661 for an ablation frequency of 915 MHz. With respect to FIG. 6B, an average 451 of trend lines 452 may be expressed as a quadratic relationship $y=-0.0131x^2-1.1106x+52.149$, which yields an $R^2$ value of about 0.9673 for an ablation frequency of 2.45 GHz.

Figure 7B:
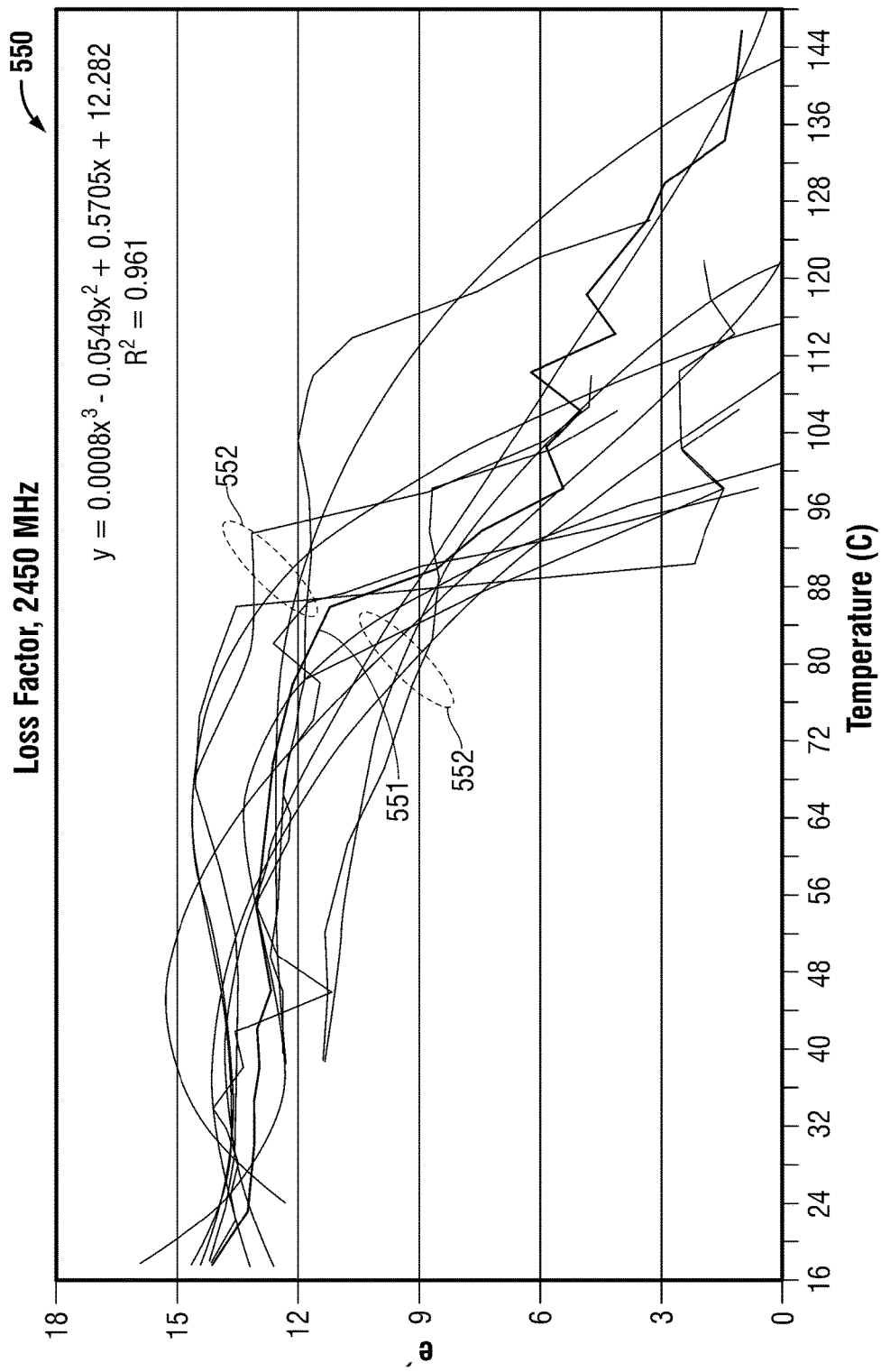
FIG. 7B illustrates a relationship between loss factor and temperature at an ablation frequency of 2.45 GHz in accordance with an embodiment of the present disclosure.

Relationships between loss factor and tissue temperature are illustrated in 7A, which depicts the relationships at an ablation frequency of 915 MHz, and FIG. 7B, which depicts the relationships at an ablation frequency of 2.45 GHz. As shown in FIG. 7A, a series of test ablations yields a set of trend lines 502. The inventors have determined that an average 501 of loss factor trend lines 502 may be expressed as a cubic relationship $y=0.0026x^3-0.1743x^2+2.6247x+11.97$, which yields an R2 of about 0.9446 for an ablation frequency of 915 MHz. With respect to FIG. 7B, an average 551 of trend lines 552 may be expressed as a cubic relationship $y=0.0008x^3-0.0549x^2+0.5704x+12.282$, which yields an $R^2$ value of about 0.9610 for an ablation frequency of 2.45 GHz.

During use, tissue sensor probe 200 is positioned at a boundary of the operative site that corresponds to an outer limit of the desired ablation region. As ablation energy is applied to targeted tissue (e.g., generator 20 is activated and ablation probe 100 is applied to the operative site), sensor probe 200 provides tissue parameters (e.g., temperature and dielectric properties) to controller 30. As the ablated region expands, controller 30 continues to monitor tissue status at the probed location. When a tissue terminal status is detected (e.g., tissue is "cooked"), controller 30 causes generator 20 to be deactivated, thus enabling a surgeon to perform a precisely-formed ablation, which may lead to improved operative outcomes, reduced operative and/or recovery times, and enhanced patient satisfaction. A distal end 213 of tissue sensor probe 200 may be generally positioned coincident with a plane radially extending transversely from feed point 122 of ablation probe 100.

Tissue sensor probe 200 may be positioned between an ablation region and an adjacent anatomical structure, which may be a critical structure to be protected from receipt of excessive ablation energy, increased temperature, and/or undesired denaturization which may occur as a side effect of an ablation procedure. In this instance, a tissue terminal status may reflect a threshold at which an ablation procedure is suspended in order to protect a critical structure from damage.

The described embodiments of the present disclosure are intended to be illustrative rather than restrictive, and are not intended to represent every embodiment of the present disclosure. Further variations of the above-disclosed embodiments and other features and functions, or alternatives thereof, may be made or desirably combined into many other different systems or applications without departing from the spirit or scope of the disclosure as set forth in the following claims both literally and in equivalents recognized in law. The claims can encompass embodiments in hardware, software, or a combination thereof.

What is claimed is:

1. A method of operating an ablation system, comprising:
   sensing tissue temperature, tissue permittivity, and tissue loss factor at a tissue sensor probe coupled to a source of ablation energy, the tissue sensor probe being disposed within tissue;
   absorbing moisture from the tissue sensor probe using an absorbent sleeve slidably disposed on the tissue sensor probe;
   determining a tissue status based on the sensed tissue temperature, the tissue permittivity, and the tissue loss factor; and
   applying ablation energy to the tissue based on the determined tissue status.

2. The method according to claim 1, wherein sensing of the tissue permittivity and the tissue loss factor occurs during a sensing phase at which no ablation energy is applied to the tissue.

3. The method according to claim 2, wherein the ablation energy is applied during a treatment phase.

4. The method according to claim 3, further comprising:
   adjusting a time period of the treatment phase using a cycle timer.

5. The method according to claim 4, wherein sensing of the tissue temperature occurs during at least one of the sensing phase or the treatment phase.

6. The method according to claim 3, further comprising:
   iterating the sensing phase and the treatment phase until the determined tissue status is indicative of a completed ablation.

7. The method according to claim 1, further comprising:
   accessing a look-up table stored in a memory associated with the source of ablation energy to determine the tissue status based on the sensed tissue temperature, the tissue permittivity, and the tissue loss factor.

8. The method according to claim 7, wherein the look-up table is a three-dimensional lookup table storing the tissue temperature, the tissue permittivity, and the tissue loss factor as each of the dimensions.

* * * * *